(12) United States Patent
Baba et al.

(10) Patent No.: US 9,585,771 B2
(45) Date of Patent: Mar. 7, 2017

(54) ELECTRICALLY DRIVEN ARTIFICIAL HAND

(71) Applicant: TOYODA GOSEI CO., LTD., Kiyosu-shi, Aichi-ken (JP)

(72) Inventors: Kazumasa Baba, Kiyosu (JP); Hiromitsu Takeuchi, Kiyosu (JP)

(73) Assignee: TOYODA GOSEI CO., LTD., Aichi-pref. (JP)

( * ) Notice: Subject to any disclaimer, the term of this patent is extended or adjusted under 35 U.S.C. 154(b) by 147 days.

(21) Appl. No.: 14/435,469

(22) PCT Filed: Oct. 11, 2013

(86) PCT No.: PCT/JP2013/077762
§ 371 (c)(1),
(2) Date: Apr. 14, 2015

(87) PCT Pub. No.: WO2014/073326
PCT Pub. Date: May 15, 2014

(65) Prior Publication Data
US 2015/0297367 A1 Oct. 22, 2015

(30) Foreign Application Priority Data
Nov. 7, 2012 (JP) .................. 2012-245461

(51) Int. Cl.
*A61F 2/54* (2006.01)
*A61F 2/70* (2006.01)
(Continued)

(52) U.S. Cl.
CPC ............... *A61F 2/70* (2013.01); *A61F 2/583* (2013.01); *A61F 2/586* (2013.01); *A61F 2/68* (2013.01);
(Continued)

(58) Field of Classification Search
CPC .... A61F 2/583; A61F 2/586; A61F 2002/587; B25J 15/0009; B25J 15/083
(Continued)

(56) References Cited

U.S. PATENT DOCUMENTS

2006/0131908 A1\* 6/2006 Tadano .................... B25J 9/104
294/111
2009/0127979 A1 5/2009 Takeuchi et al.

FOREIGN PATENT DOCUMENTS

CN 101919755 A 12/2010
JP 2003-305069 A 10/2003
(Continued)

OTHER PUBLICATIONS

International Preliminary Report on Patentability mailed May 12, 2015 in corresponding international application No. PCT/JP2013/077762 (English translation only).
(Continued)

*Primary Examiner* — David H Willse
(74) *Attorney, Agent, or Firm* — Posz Law Group, PLC (57) ABSTRACT

Finger parts flex and extend about joint sections. A wire is arranged along each finger part through the joint sections. A motor winds the wires to pull the wires in the flexing direction and cause the finger parts to flex. A polymer actuator arranged to correspond to a part of each wire is formed in an elongated shape of a polymer material and elastically deforms in response to an application of voltage and performs extension and contraction in the axial direction by being restored to the original shape in response to stoppage of the voltage application. A lock mechanism restricts relative movement between the wire and the motor after the wire has been wound up by the motor. The polymer actuator performs extension and contraction while relative
(Continued)

movement is restricted by the lock mechanism, thereby pulling the wire in the flexing direction.

8 Claims, 5 Drawing Sheets

(51) Int. Cl.
    *A61F 2/58*    (2006.01)
    *A61F 2/68*    (2006.01)
    *B25J 15/00*   (2006.01)
    *B25J 15/08*   (2006.01)
    *A61F 2/50*    (2006.01)

(52) U.S. Cl.
    CPC ... *B25J 15/0009* (2013.01); *A61F 2002/5073* (2013.01); *A61F 2002/5093* (2013.01); *A61F 2002/6854* (2013.01); *A61F 2002/701* (2013.01); *B25J 15/083* (2013.01)

(58) Field of Classification Search
    USPC .......................................................... 623/64
    See application file for complete search history.

(56) References Cited

FOREIGN PATENT DOCUMENTS

| JP | 2009-083020 A | 4/2009 |
|---|---|---|
| JP | 2009-124875 A | 6/2009 |
| JP | 2011-152620 A | 8/2011 |

OTHER PUBLICATIONS

International Search Report of the International Searching Authority mailed Dec. 17, 2013 for the corresponding international application No. PCT/JP2013/077762 (and English translation).

Office Action dated Jan. 18, 2016 issued in corresponding CN patent application No. 201380056111.8 (and English translation).

* cited by examiner

Fig.6C

ELECTRICALLY DRIVEN ARTIFICIAL HAND

CROSS REFERENCE TO RELATED APPLICATIONS

This application is a U.S. national stage application of PCT/JP2013/077762 filed on Oct. 11, 2013, which is based on and claims priority to Japanese Patent Application No. 2012-245461 filed on Nov. 7, 2012, the contents of which are incorporated herein by reference.

BACKGROUND

The present invention relates to an electric prosthetic hand with finger parts to be flexed and extended using a driving source to operate in response to passage of a current.

Various types of electric prosthetic hands have been developed. In these prosthetic hands, a motor to operate in response to passage of a current is used as a driving source and rotation of the motor is transmitted via a driving mechanism to finger parts to flex and extend these finger parts, thereby grasping a target object with the finger parts (see Patent Document 1, for example). A compact motor is used as the drive source in consideration of the mountability on an electric prosthetic hand.

PRIOR ART DOCUMENTS

Patent Documents

Patent Document 1: Japanese Laid-Open Patent Publication No. 2003-305069

SUMMARY

As described above, an electric prosthetic hand using a motor as a driving source can grasp a target object by largely flexing or displacing the finger parts. However, compact motors can generate only low torque. This makes it difficult to stably grasp a target object with the finger parts.

Accordingly, it is an objective of the present invention to provide an electric prosthetic hand capable of stably grasping a target object while utilizing the benefits of a motor capable of largely displacing the finger parts.

To achieve the foregoing objective, and in accordance with one aspect of the present invention, an electric prosthetic hand is provided that includes a plurality of finger parts, each of which is flexed and extended about a joint section, a wire arranged along each of the finger parts while passing through the joint section, a motor that winds up the wire to pull the wire along a length of the wire in a direction of flexing, thereby flexing the finger part, a polymer actuator, and a locking mechanism. The polymer actuator is formed of a polymer material into an elongated shape and arranged to correspond to a part of the wire. The polymer actuator expands and contracts in an axial direction by being deformed elastically in response to application of a voltage and restoring its original shape in response to stopping the application of the voltage. The locking mechanism restricts relative movement between the wire and one of the motor and the polymer actuator after the wire is wound up by the motor. The polymer actuator expands and contracts when the locking mechanism restricts the relative movement, thereby pulling the wire in the flexing direction.

According to the aforementioned structure, when the finger parts are flexed to grasp a target object, the motor and the polymer actuator are used as driving sources.

When the output shaft of the motor is rotated to wind the wire, the wire is pulled in the flexing direction. The movement of the wire is transmitted via the joint section to each section of each finger part, thereby flexing this finger part about the joint section.

In contrast, the polymer actuator arranged to correspond to a part of the wire expands and contracts in the axial direction by being deformed elastically in response to application of a voltage and restoring its original shape in response to stopping application of a voltage.

After the wire is wound up by the motor, the locking mechanism restricts relative movement between the wire and one of the motor and the polymer actuator. The aforementioned expansion and contraction of the polymer actuator is done while the locking mechanism restricts the relative movement. This expansion and contraction pulls the wire further in the flexing direction. The movement of the wire is transmitted via the joint section to each section of each finger part, thereby flexing this finger part further about the joint section.

The motor has a feature of generating a large displacement and low output torque. The polymer actuator has a feature of generating a small displacement and high output torque.

Thus, each finger part can be flexed or displaced largely by pulling the wire to a large extent in the flexing direction by the motor. Meanwhile, each finger part can be pressed against a target object by a strong force to grasp the target object by pulling the wire in the flexing direction by a strong force by the polymer actuator. By doing so, the feature of the motor is compensated for by the polymer actuator. Thus, the motor is responsible for flexing or displacing the finger parts to a position near a target object. The polymer actuator is responsible for grasping the target object with the finger parts. As a result, a target object is grasped stably by utilizing the benefit of the motor capable of displacing the finger parts largely.

Even if a force of pulling the wire in a direction opposite to the flexing direction acts on the wire wound up by the motor and is pulled in the flexing direction by the polymer actuator, the locking mechanism restricts movement of the wire in this opposite direction. As a result, a target object continues to be grasped with the finger parts.

In the above described electric prosthetic hand, the locking mechanism permits rotation of the motor in a winding direction when the wire is wound by the motor and restricts relative movement between the wire and the motor by restricting rotation of the motor in a direction opposite to the winding direction after the wire is wound up by the motor. The polymer actuator is fixed to the wire. The polymer actuator is expanded when the wire is wound by the motor and is contracted when the locking mechanism restricts the relative movement.

In the aforementioned structure, the locking mechanism permits rotation of the motor in the winding direction while the wire is wound by the motor. This rotation pulls the wire in the flexing direction, thereby moving the wire toward the motor.

At this time, the polymer actuator fixed to the wire expands. This moves the polymer actuator in an expanded state in the flexing direction together with the wire. The aforementioned movement of the wire is transmitted via the joint section to each section of each finger part, thereby flexing or displacing the finger parts about the joint sections largely to a position near a target object.

After the wire is wound up by the motor, the locking mechanism restricts rotation of the motor in a direction opposite to the winding direction to restrict relative movement between the wire and the motor. The polymer actuator contracts while this relative movement is restricted. The polymer actuator in a contracted state pulls the wire further in the flexing direction with respect to the longitudinal direction. The movement of the wire is transmitted via the joint section to each section of each finger part, thereby flexing this finger part further about the joint section. The finger parts are pressed against the target object by a strong force to grasp this target object stably.

In the above described electric prosthetic hand, the wire is arranged to be movable along the length of the wire relative to the polymer actuator, and the polymer actuator has a fixed end at an end portion near the finger part with respect to the axial direction and a movable end at an end portion near the motor with respect to the axial direction. The locking mechanism permits relative movement between the wire and the polymer actuator by not securing the wire to the movable end when the wire is wound by the motor. The locking mechanism restricts relative movement between the wire and the polymer actuator by securing the wire to the movable end after the wire is wound up by the motor. The polymer actuator is contracted when the wire is wound by the motor and is expanded when the locking mechanism restricts the relative movement.

In the aforementioned structure, while the wire is wound by the motor, the wire is pulled in the flexing direction. At this time, the polymer actuator contracts to make the movable end of the polymer actuator (the end portion near the motor) approach the fixed end thereof (the end portion near the finger part). The locking mechanism does not secure the wire to the movable end. This permits relative movement between the wire and the polymer actuator, thereby moving the wire toward the motor. This movement of the wire is transmitted via the joint section to each section of each finger part, thereby flexing or displacing the finger parts about the joint sections largely to a position near a target object.

After the wire is wound up by the motor, the locking mechanism secures the wire to the movable end of the polymer actuator. This restricts relative movement between the wire and the polymer actuator. The polymer actuator expands while this relative movement is restricted. In response to this expansion, the movable end of the polymer actuator (the end portion near the motor) separates farther from the fixed end thereof (the end portion near the finger part). The wire is pulled further in the flexing direction with the movable end of the polymer actuator. The movement of the wire is transmitted via the joint section to each section of each finger part, thereby flexing this finger part further about the joint section. The finger parts are pressed against a target object by a strong force to grasp this target object stably.

In the above described electric prosthetic hand, the wire is arranged so as to be movable along the length of the wire relative to the polymer actuator, and the motor is arranged to be movable along the length of the wire. The polymer actuator has a fixed end at an end portion near the finger part with respect to the axial direction and a movable end at an end portion near the motor with respect to the axial direction. The locking mechanism permits rotation of the motor in a direction of winding when the wire is wound up by the motor. The locking mechanism restricts relative movement between the wire and the motor by restricting rotation of the motor in a direction opposite to the winding direction after the wire is wound up by the motor. The polymer actuator is contracted when the wire is wound by the motor, and the polymer actuator is expanded when the locking mechanism restricts the relative movement, and the expansion of the polymer actuator moves the motor in the flexing direction.

In the aforementioned structure, while the wire is wound by the motor, the locking mechanism permits rotation of the motor in the winding direction. This pulls the wire in the flexing direction, thereby moving the wire toward the motor. At this time, the polymer actuator contracts to make the movable end of the polymer actuator approach the fixed end thereof. This movement of the wire is transmitted via the joint section to each section of each finger part, thereby flexing or displacing the finger parts largely about the joint sections to a position near a target object.

After the wire is wound up by the motor, the locking mechanism restricts rotation of the motor in a direction opposite to the winding direction, thereby restricting relative movement between the wire and the motor. The polymer actuator expands while this relative movement is restricted. In response to this expansion, the movable end of the polymer actuator separates farther from the fixed end thereof to move the wire in the flexing direction.

Thus, the wire is pulled further in the flexing direction. The movement of the wire is transmitted via the joint section to each section of each finger part, thereby flexing this finger part further about the joint section. The finger parts are pressed against a target object by a strong force to grasp this target object stably.

In the above described electric prosthetic hand, the polymer actuator includes a dielectric layer made of an insulating polymer material with elasticity and electrodes in a pair that are made of a conductive polymer material with elasticity and sandwich the dielectric layer from opposite sides. The polymer actuator expands and contracts by expanding the dielectric layer along a surface of the dielectric layer in response to application of a voltage between the electrodes and contracting the dielectric layer to restore its original shape in response to stopping the voltage application.

In the aforementioned structure, in response to application of a voltage between the electrodes, one of the electrodes is charged positive and the other electrode is charged negative. A current continues to flow until a charge of a given amount is accumulated in each electrode. Substantially no current flows in response to accumulation of the charge of the given amount. This reduces the power to be consumed by the expansion and contraction of the polymer actuator.

If the electrodes are charged in the aforementioned way, a force of making the positive and negative charges attract each other (Coulomb force) acts on the electrodes to press the dielectric layer with the electrodes from the opposite sides. The dielectric layer is made of an insulating polymer material with elasticity. Thus, when the dielectric layer is pressed with the electrodes from the opposite sides, the dielectric layer expands along a surface of the dielectric layer. The electrodes are made of a conductive polymer material also with elasticity, so that they expand in pursuit of the dielectric layer.

When application of a voltage to the electrodes is stopped, the charge accumulated in each electrode is emitted. This reduces the charge of each electrode, thereby reducing the aforementioned Coulomb force. As a result, the dielectric layer contracts along the surface of the dielectric layer by its elastic resilience. The electrodes with elasticity contract in pursuit of the dielectric layer.

In the above described electric prosthetic hand, the polymer actuator is formed into a cylindrical shape by winding the dielectric layer and the electrodes in a spiral pattern, and the polymer actuator expands in the axial direction in response to application of a voltage between the electrodes and contracts in the axial direction in response to stopping the voltage application to restore its original shape.

In the aforementioned structure, the polymer actuator has a compact cylindrical shape formed by winding the dielectric layer and the electrodes on the opposite sides of the dielectric layer in a spiral pattern. This improves the mountability of the polymer actuator to the electric prosthetic hand.

In response to application of a voltage between the electrodes, the cylindrical polymer actuator expands in the axial direction (the axial direction of the polymer actuator), which is a direction along the surface of the dielectric layer. In response to stopping application of a voltage between the electrodes, the polymer actuator contracts in the axial direction to restore its original shape.

In the above described electric prosthetic hand, the polymer actuator is one of a plurality of polymer actuators, and the movable ends of the polymer actuators are attached to a common attachment part.

In the aforementioned structure, multiple polymer actuators are used and respective movable ends of the polymer actuators are attached to the common attachment part. This applies a large force on the attachment part. As a result, the large force is transmitted to each finger part via the attachment part.

In the above described electric prosthetic hand, at least one of the finger parts has a plurality of joint sections, and the wire, which is driven by the motor and the polymer actuator, is arranged in the finger part with the joint sections while passing through the joint sections.

In an electric prosthetic hand of a type of flexing a finger part by pulling a wire, the greater number of joint sections of the finger part, the greater the amount by which the wire needs to be pulled for flexing the finger part at each joint section. Thus, by applying the aforementioned electric prosthetic hand of pulling the wire in the flexing direction using the motor and the polymer actuator in combination to an electric prosthetic hand of flexing a finger part with multiple joint sections with a wire, the advantage of grasping a target object stably can be achieved more effectively while utilizing the benefit of the motor, which is capable of displacing the finger part largely.

The aforementioned electric prosthetic hand is capable of grasping a target object stably while utilizing the benefit of a motor capable of displacing a finger part largely.

DETAILED DESCRIPTION OF THE PREFERRED EMBODIMENTS

First Embodiment

An electric prosthetic hand according to a first embodiment will be described with reference to FIGS. 1 to 4.

Figure 1:
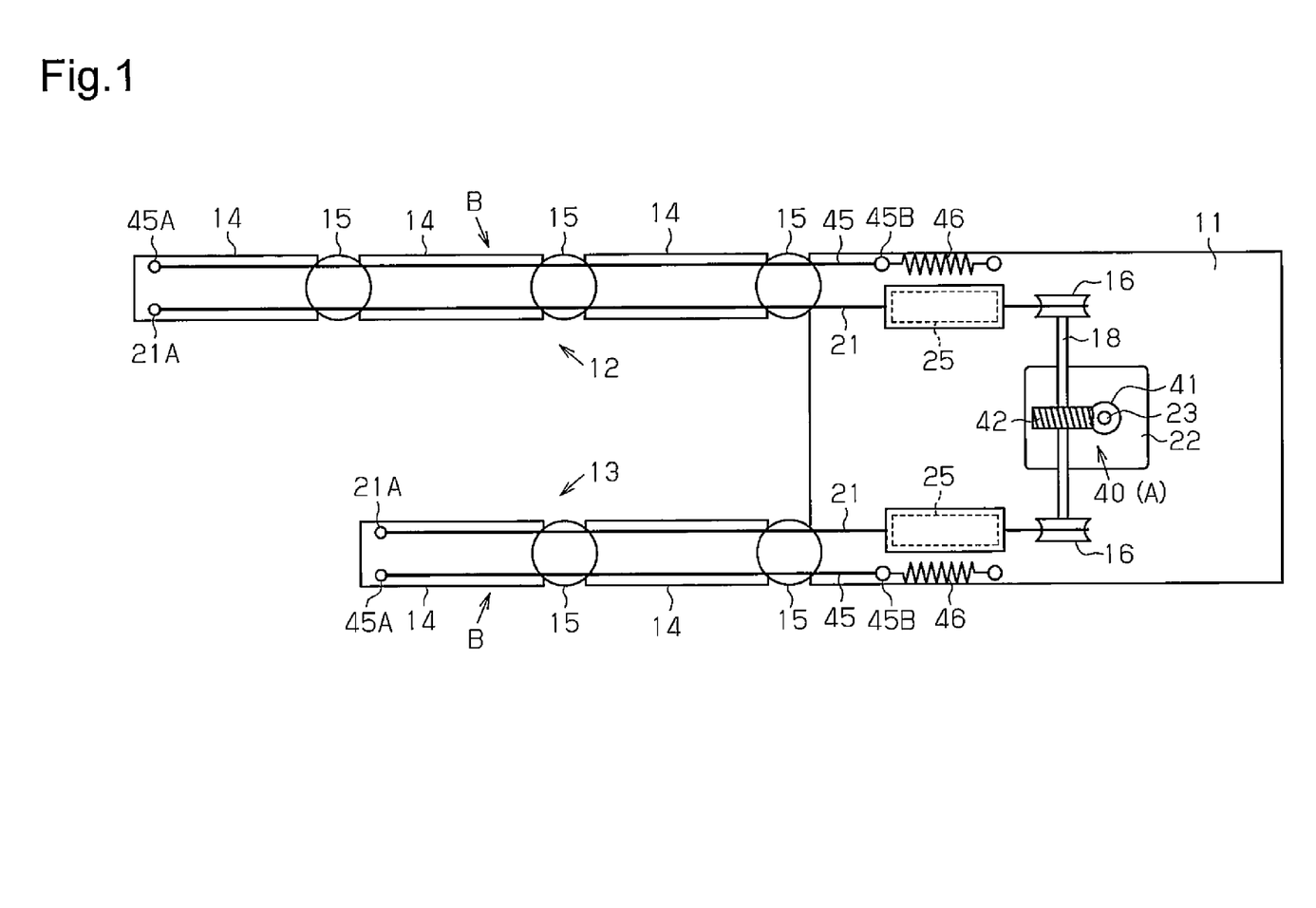
FIG. 1 is a schematic diagram of an electric prosthetic hand according to a first embodiment, showing the entire structure of the electric prosthetic hand.

As shown in FIG. 1, the electric prosthetic hand includes a prosthetic hand body 11, finger parts 12 and 13, wires 21 provided for each of the finger parts 12 and 13, a driving source, a locking mechanism A, and paying-out mechanism B provided for each of the finger parts 12 and 13.

The prosthetic hand body 11 corresponds to the back of a human hand and forms the frame of the electric prosthetic hand. Each of the finger parts 12 and 13 has movable sections 14 and joint sections 15. The movable sections 14 are arranged to form a line in a direction corresponding to the length of the movable sections 14. A side of each of the finger parts 12 and 13 near the prosthetic hand body 11 is referred to as a proximal end. A side of each of the finger parts 12 and 13 away from the prosthetic hand body 11 is referred to as a distal end. One of the joint sections 15 is arranged between the prosthetic hand body 11 and the movable section 14 nearest the prosthetic hand body 11. The other joint sections 15 are each arranged between adjacent ones of the movable sections 14. Each movable section 14 can be flexed about the joint section 15 contacting the proximal end portion of this movable section 14.

The prosthetic hand body 11 includes pulleys 16 each provided for one of the finger parts 12 and 13. Each pulley 16 is fixed to a common rotary shaft 18 perpendicular to the longitudinal direction of each of the finger parts 12 and 13. The pulley 16 rotates integrally with the rotary shaft 18.

The wire 21 provided for each of the finger parts 12 and 13 corresponds to the tendon of a finger of a human being. The wire 21 is arranged to extend along the length of each of the finger parts 12 and 13 while passing through each joint section 15. A distal end portion 21A of each wire 21 is secured to a distal end portion of the movable section 14 nearest the distal end. Each wire 21 is arranged to pass through all the movable sections 14 and all the joint sections 15. A proximal end portion of each wire 21 is secured to the pulley 16.

The driving source pulls the wires 21 to the right as viewed in FIG. 1, specifically in a direction of flexing the finger parts 12 and 13. The driving source is formed of a motor 22 common to the finger parts 12 and 13 and polymer actuators 25 each provided for one of the finger parts 12 and 13.

An electric motor to rotate an output shaft 23 in response to passage of a current is used as the motor 22. The motor 22 is firmly fixed to the prosthetic hand body 11. Changing the mode of passage of a current allows the motor 22 to rotate forward or backward. The output shaft 23 of the motor 22 extends in a direction perpendicular to the rotary shaft 18, specifically in a direction perpendicular to the sheet of FIG. 1. The output shaft 23 is coupled via a worm gear mechanism 40 to the rotary shaft 18. The motor 22 rotates the output shaft 23 in one direction to rotate both pulleys 16 in a direction for winding the wires 21. The motor 22 can rotate both pulleys 16 in a direction for paying out the wire 21 by rotating the output shaft 23 in a direction opposite to the aforementioned direction.

Each polymer actuator 25 pulls the corresponding wire 21 in the flexing direction after this wire 21 is wound up by the motor 22. The polymer actuator 25 is formed of a polymer material and deforms elastically in response to application of a voltage. The polymer actuator 25 restores its original shape in response to stopping application of a voltage. In this way, the polymer actuator 25 expands and contracts.

Each polymer actuator 25 may be an actuator of what is referred to as a dielectric type or an ionic type. In this embodiment, the polymer actuator 25 employs a dielectric type exhibiting excellence in terms of displacement and generative force, for example.

Figure 2:
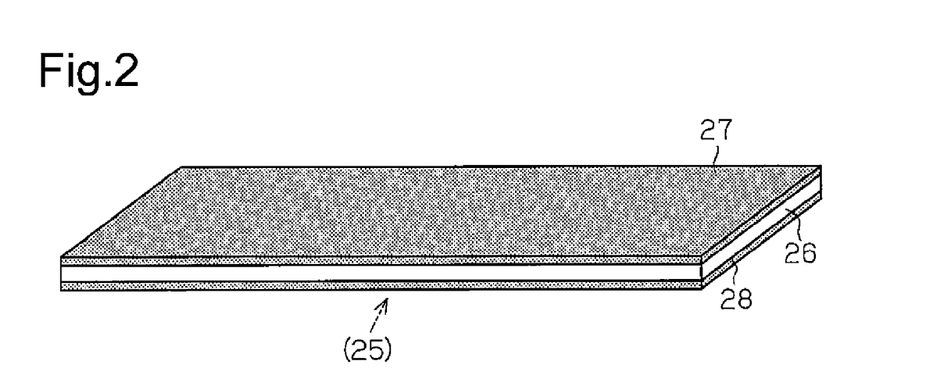
FIG. 2 is a perspective view of the structure of a polymer actuator in a developed state of the first embodiment.

FIG. 2 shows the polymer actuator 25 of a dielectric type in a developed state in a plate-like form. As shown in FIG. 2, the polymer actuator 25 includes a dielectric layer 26 made of an insulating polymer material with elasticity and electrodes 27 and 28 in a pair that are made of a conductive polymer material with elasticity and sandwich the dielectric layer 26 from the opposite sides with respect to the thickness direction (the vertical direction of FIG. 2) of the dielectric layer 26.

The dielectric layer 26 is made of a polymer compound (such as a polymer gel) having movable crosslinking points. As an example, the dielectric layer 26 is made of polyrotaxane. In contrast, the electrodes 27 and 28 are made of general-purpose rubber, for example.

In response to application of a voltage between the electrodes 27 and 28, the dielectric layer 26 expands along a surface of the dielectric layer 26. In response to stopping application of a voltage, the dielectric layer 26 contracts to restore its original shape. In this way, the polymer actuator 25 expands and contracts.

Figure 3A:
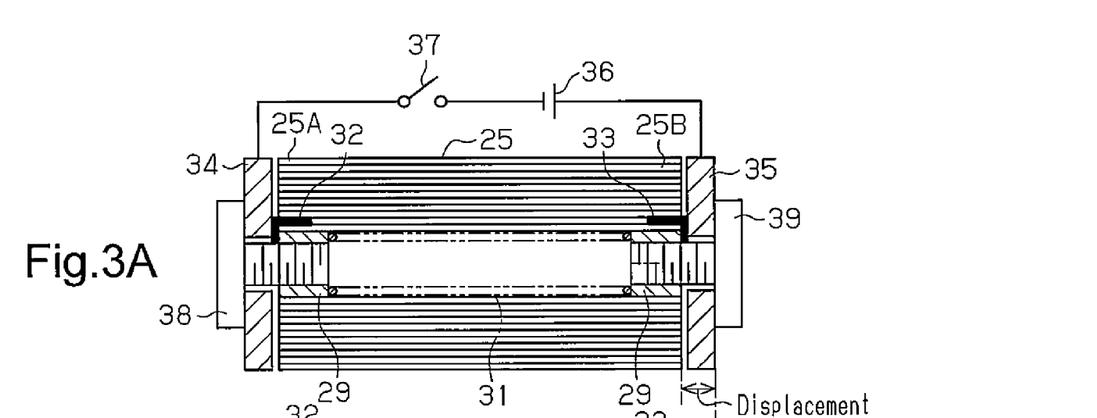
FIG. 3A is a cross-sectional view of the polymer actuator of the first embodiment, showing the internal structure of the polymer actuator having contracted in response to stopping application of a voltage.
Figure 3B:
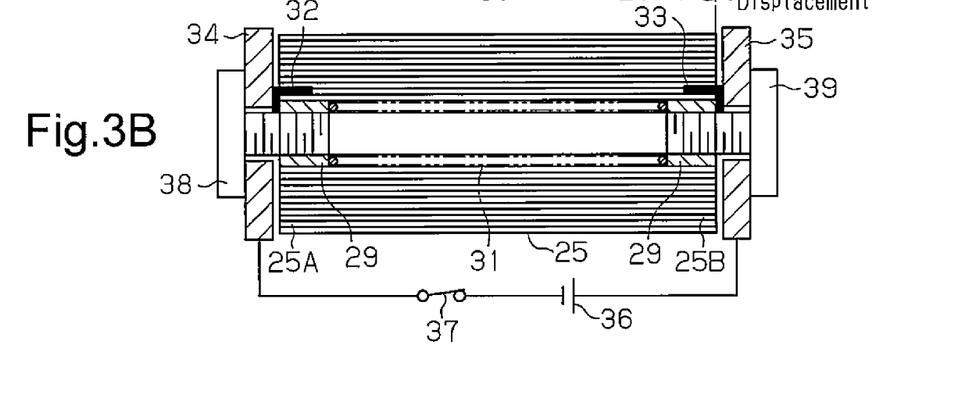
FIG. 3B is a cross-sectional view of the polymer actuator of the first embodiment, showing the internal structure of the polymer actuator having expanded in response to application of a voltage.

The dielectric layer 26 and the electrodes 27 and 28 are wound in a spiral pattern to form an elongated cylindrical shape with open opposite ends, thereby forming a principal part of the polymer actuator 25 as shown in FIGS. 3A and 3B. Such a compact shape of the polymer actuator 25 allows the polymer actuator 25 to be readily mounted on the electric prosthetic hand.

In response to application of a voltage between the electrodes 27 and 28, each polymer actuator 25 expands in the axial direction of the dielectric layer 26, specifically in the longitudinal direction of the polymer actuator 25 (see FIG. 3B). In response to stopping application of a voltage, the polymer actuator 25 contracts in this axial direction (the longitudinal direction) to restore its original shape (see FIG. 3A). In this way, the polymer actuator 25 expands and contracts in the axial direction in response to application of a voltage and stopping application of a voltage.

A cylindrical internal screw member 29 is inserted in each of opposite openings of the polymer actuator 25 with respect to the axial direction and fixed to the corresponding opening. An internal thread is formed on the inner wall surface of each screw member 29.

A coil spring 31 is arranged in a compressed state inside each polymer actuator 25 and between the internal screw members 29. Each coil spring 31 biases the internal screw members 29 away from each other (to the right and to the left as viewed FIGS. 3A and 3B). The biasing force of the coil spring 31 is transmitted via the internal screw members 29 to the polymer actuator 25. Thus, the polymer actuator 25 is biased to expand in the axial direction of the polymer actuator 25. This structure is intended to increase the displacement of the polymer actuator 25 in the axial direction as much as possible by minimizing expansion of the dielectric layer 26 in a direction along the spiral when the dielectric layer 26 is expanded in the direction along the surface of the dielectric layer 26.

Figure 4A:
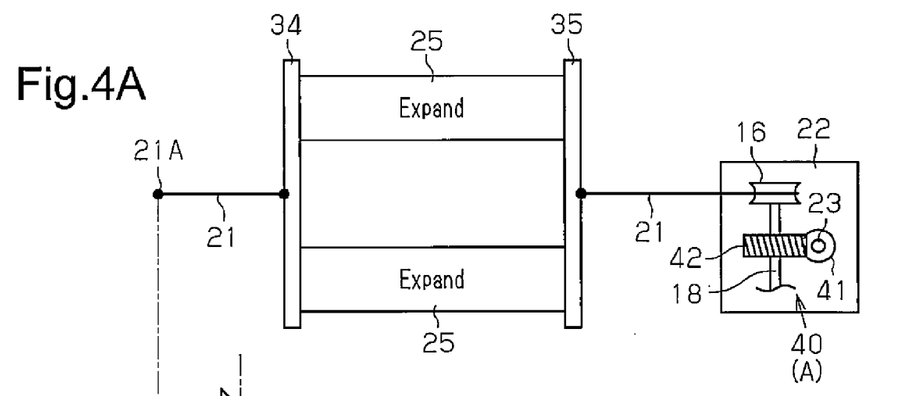
FIGS. 4A to 4C are schematic diagrams showing behavior of the electric prosthetic hand of the first embodiment.
Figure 4B:
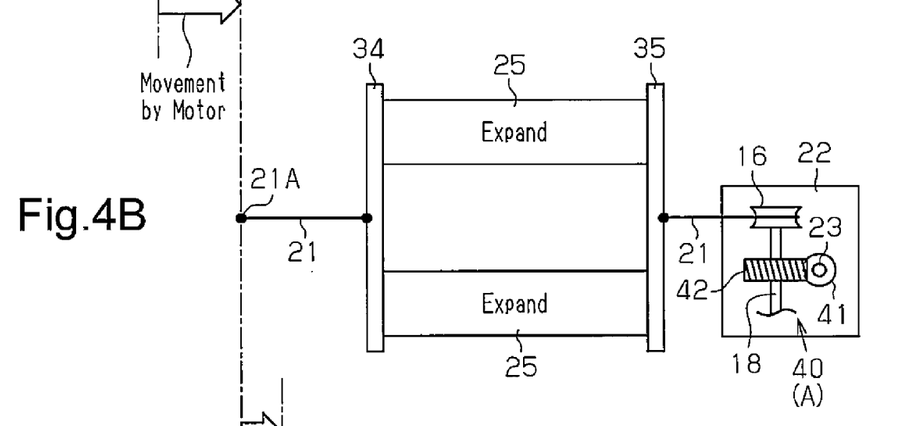
Figure 4C:
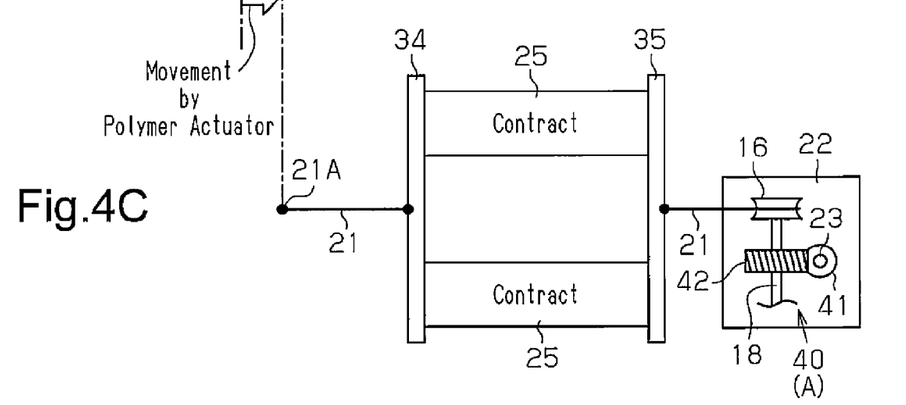

As shown in FIG. 4A, a plurality of the polymer actuators 25 of the aforementioned structure is used. For illustrative purposes, two polymer actuators 25 are shown in FIGS. 4A to 4C. However, the number of the polymer actuators 25 is not limited to two. In FIG. 1, only one polymer actuator 25 is shown to be provided for each of the finger parts 12 and 13. The polymer actuators 25 are arranged in parallel while the axial directions of the polymer actuators 25 are aligned with the longitudinal direction of each of the finger parts 12 and 13 in an extended state. Specifically, a direction in which each polymer actuator 25 expands and contracts agrees with the longitudinal direction of each of the finger parts 12 and 13 in an extended state. Each polymer actuator 25 has movable ends at opposite end portions with respect to the direction of its length.

As shown in FIGS. 3A and 3B, an electrode lead-out part 32 and an electrode lead-out part 33 are provided at the opposite end portions of each polymer actuator 25. The left electrode lead-out part 32 is electrically connected to a first electrode in the electrodes 27 and 28. The right electrode lead-out part 33 is electrically connected to a second electrode in the electrodes 27 and 28.

Plate shaped attachment parts 34 and 35 are provided on the opposite sides of each polymer actuator 25 with respect to the axial direction. The attachment parts 34 and 35 are arranged to face each other with the aforementioned polymer actuators 25 in between. The right attachment part 35 in the attachment parts 34 and 35 is connected to a positive pole of a power source 36. The left attachment part 34 is connected to a negative pole of the power source 36 via a switch 37.

A left end portion 25A of each polymer actuator 25 is fastened with a fastening member 38 such as a bolt to the left attachment part 34. The fastening member 38 presses the left electrode lead-out part 32 against the left attachment part 34, thereby electrically connecting the first electrode in the electrodes 27 and 28 to the left attachment part 34 via the left electrode lead-out part 32.

A right end portion 25B of each polymer actuator 25 is fastened with a fastening member 39 to the right attachment part 35. The fastening member 39 presses the right electrode lead-out part 33 against the right attachment part 35, thereby electrically connecting the second electrode in the electrodes 27 and 28 to the right attachment part 35 via the right electrode lead-out part 33.

As shown in FIGS. 4A to 4C, the aforementioned polymer actuators 25 are provided to correspond to a part of each wire 21 in a posture parallel to this wire 21. The attachment parts 34 and 35 are provided in parts of the wire 21 in a state perpendicular to this wire 21. The attachment parts 34 and 35 are fixed to the wire 21.

The aforementioned polymer actuators 25 and the attachment parts 34 and 35 are not fixed to the prosthetic hand body 11 and are movable in the longitudinal direction of the wire 21 together with this wire 21.

The motor 22 has a feature of generating a large displacement and low output torque. Each polymer actuator 25 has a feature of generating a small displacement and high output torque.

By using this difference between the features, if each of the finger parts 12 and 13 in an extended state is to be flexed or displaced largely, the wire 21 is pulled to a large extent by the motor 22. In contrast, if a target object (not shown in the drawings) is to be grasped with the finger parts 12 and 13 by pressing the finger parts 12 and 13 against the target object by a strong force, the wire 21 is pulled in the flexing direction by a strong force by each polymer actuator 25. By doing so, the feature of the motor 22 is compensated for by each polymer actuator 25. Specifically, the motor 22 is responsible for flexing or displacing the finger parts 12 and 13 in their extended states to a position near a target object. Each polymer actuator 25 is responsible for grasping a target object with the finger parts 12 and 13.

As shown in FIG. 1, the locking mechanism A restricts relative movement between the wire 21 and the motor 22 after this wire 21 is wound up by the motor 22. The locking mechanism A satisfies the following conditions:

Condition 1: to permit rotation of the motor 22 in a winding direction while the wire 21 is wound by the motor 22.

Condition 2: to restrict relative movement between the wire 21 and the motor 22 by restricting rotation of the motor 22 in a direction opposite to the winding direction after the wire 21 is wound up by the motor 22.

The worm gear mechanism 40 formed of a worm 41 and a worm wheel 42 is used as the locking mechanism A satisfying Conditions 1 and 2.

More specifically, the rotary shaft 18 of the pulleys 16 is perpendicular to the output shaft 23 of the motor 22. The worm 41 is formed of a screw gear such as a cylindrical or hourglass gear and is arranged on the output shaft 23 of the motor 22 in a manner that allows the worm 41 to rotate integrally with the output shaft 23. The worm wheel 42 is formed of a helical gear and is arranged on the rotary shaft 18 in a manner that allows the worm wheel 42 to rotate integrally with the rotary shaft 18. The worm wheel 42 is in meshing engagement with the worm 41.

The worm gear mechanism 40 is generally used to transmit rotation of a high reduction ratio between two shafts (the rotary shaft 18 and the output shaft 23) perpendicular to each other but not intersecting each other. The worm gear mechanism 40 characteristically involves a large load for rotating the worm 41 by the worm wheel 42.

The paying-out mechanism B is to pay out the wire 21 wound up around the pulley 16 by the motor 22 in a direction opposite to the direction in which the motor 22 pulls the wire 21 (the flexing direction), thereby extending each of the finger parts 12 and 13 in a flexed state. Each paying-out mechanism B includes a wire 45 and a return spring 46 provided for a corresponding one of the finger parts 12 and 13.

The wire 45 for each of the finger parts 12 and 13 is arranged to extend along the length of the finger parts 12 and 13, while passing through each joint section 15. A distal end portion 45A of each wire 45 is secured to a distal end portion of the movable section 14 nearest the distal end. The wire 45 is arranged to pass through all of the movable sections 14 and all of the joint sections 15. A proximal end portion 45B of the wire 45 is coupled to a return spring 46. Each return spring 46 biases the wire 45 in a direction opposite to the direction in which the motor 22 pulls the wire 21 (the flexing direction), specifically in a direction for extending the finger parts 12 and 13.

During winding of the wire 21 by the motor 22, a voltage is applied between the electrodes 27 and 28 to make each polymer actuator 25 expand. While the locking mechanism A restricts relative movement between the wire 21 and the motor 22, application of a voltage between the electrodes 27 and 28 is stopped to make each polymer actuator 25 contract.

The structure of the electric prosthetic hand of the first embodiment is as described above. Operation of this electric prosthetic hand will now be described.

FIGS. 1 and 4A show a state immediately before a target object is grasped with the electric prosthetic hand. In this state, the wire 21 is wound up by the motor 22 to a minimum amount. No current is passed through the motor 22. The wire 21 is pulled by the paying-out mechanism B (the wire 45 and the return spring 46) in a direction opposite to the direction in which the motor 22 pulls the wire 21 (the flexing direction). Each of the finger parts 12 and 13 is in an extended state.

As shown in FIG. 3B, the switch 37 is closed. A voltage is applied between the electrodes 27 and 28 of each polymer actuator 25 (see FIG. 2). One of the electrodes 27 and 28 is charged positive and the other electrode is charged negative.

The force of making the positive and negative charges attract each other (Coulomb force) acts on the electrodes 27 and 28 to press the dielectric layer 26 from the opposite sides with respect to the thickness direction of the dielectric layer 26, thereby making the dielectric layer 26 expand along the surface of the dielectric layer 26. The electrodes 27 and 28 are made of a conductive polymer material also with elasticity, so that they expand in pursuit of the dielectric layer 26. Each polymer actuator 25 formed into a cylindrical shape by winding the dielectric layer 26 and the electrodes 27 and 28 in a spiral pattern expands in the axial direction (the longitudinal direction) that is a direction along the surface of the dielectric layer 26.

To grasp the target object (not shown in the drawings) with the electric prosthetic hand in the aforementioned state, the motor 22 and the polymer actuator 25 are used as a driving source.

When the motor 22 is used as a driving source, the locking mechanism A (the worm gear mechanism 40) permits rotation of the output shaft 23 in the direction in which the wire 21 is wound. When the output shaft 23 of the motor 22 is rotated, the rotation is transmitted via the worm gear mechanism 40 (the worm 41 and the worm wheel 42) to the rotary shaft 18. This rotates the pulley 16 together with the rotary shaft 18 to wind up the wire 21 around the pulley 16. Then, the wire 21 is pulled to the right, specifically in the flexing direction along the length to move the wire 21 toward the motor 22.

Each polymer actuator 25 is fixed via the attachment parts 34 and 35 to the wire 21. This moves each polymer actuator 25 in the flexing direction together with the wire 21 while keeping the polymer actuator 25 in an expanded state as shown in FIG. 4B.

This movement of the wire 21 is transmitted via each joint section 15 to each movable section 14 of each of the finger parts 12 and 13, thereby flexing each of the finger parts 12 and 13 about the joint sections 15.

As described above, the motor 22 has the feature of generating a larger displacement and lower output torque than the polymer actuator 25. Thus, the wire 21 is pulled to a large extent to flex or displace each of the finger parts 12 and 13 largely. This displacement continues until the finger parts 12 and 13 approach the target object.

After the wire 21 is wound up around the pulley 16 by the motor 22 to place each of the finger parts 12 and 13 in the aforementioned state, passage of a current through the motor 22 is stopped. In response to this stop, force of pulling the wire 21 in the flexing direction disappears. Meanwhile, force generated by the paying-out mechanism B (the wire 45 and the return spring 46), specifically, force of pulling the wire 21 in a direction opposite to the direction in which the motor 22 pulls the wire 21 (the flexing direction) acts on the wire 21. At this stage, however, the locking mechanism A (the worm gear mechanism 40) restricts rotation of the motor 22 in a direction opposite to the winding direction, thereby restricting relative movement between the wire 21 and the motor 22. Specifically, the worm gear mechanism 40 requires a large load to rotate the worm 41 with the worm wheel 42. Thus, by using the worm gear mechanism 40 as the locking mechanism A, the wire 21 is not payed out from the pulley 16 even when passage of a current through the motor 22 is stopped. As a result, the wire 21 is kept in a position where the wire 21 is wound up by the motor 22.

Under the aforementioned circumstance, where the worm gear mechanism 40 restricts relative movement between the wire 21 and the motor 22, the switch 37 is opened as shown in FIG. 3A to stop application of a voltage between the electrodes 27 and 28 of the polymer actuator 25 (see FIG. 2). In each polymer actuator 25, charge is not accumulated in the electrodes 27 and 28 as a result of discharge (charge emission). This makes each polymer actuator 25 contract as shown in FIG. 4C.

Each polymer actuator 25 placed in a contracted state in this way pulls the wire 21 further in the flexing direction. This movement of the wire 21 is transmitted via each joint section 15 to each movable section 14 of each of the finger parts 12 and 13, thereby flexing each of the finger parts 12 and 13 further about the joint sections 15.

As described above, each polymer actuator 25 has the feature of generating a smaller displacement and higher output torque than the motor 22. Thus, the wire 21 is pulled by a strong force and the finger parts 12 and 13 are pressed against the target object by a strong force, thereby grasping the target object stably.

As described above, the paying-out mechanism B (the wire 45 and the return spring 46) generates a force acting on the wire 21 wound up by the motor 22 and pulled by the polymer actuator 25 in the flexing direction with respect to the longitudinal direction. This force acts to pull the wire 21 in a direction opposite to the flexing direction. However, movement of the wire 21 in this opposite direction is restricted by the locking mechanism A (the worm gear mechanism 40), so that the target object continues to be grasped with the finger parts 12 and 13.

To move each of the finger parts 12 and 13 away from the target object, the output shaft 23 of the motor 22 is rotated in a backward direction (backward rotation) opposite to the direction in which the output shaft 23 rotates for grasping the target object. This backward rotation weakens the force of the motor 22 of pulling the wire 21. Each wire 21 is pulled with the wire 45 and the return spring 46 in a direction opposite to the direction in which the motor 22 pulls the wire 21 (the flexing direction). This extends each of the finger parts 12 and 13 to weaken the force of grasping the target object. As a result, each of the finger parts 12 and 13 moves away from the target object.

The switch 37 is closed in a period from when the aforementioned backward rotation of the motor 22 is started to a point immediately before the target object is grasped with the electric prosthetic hand again. By closing the switch 37, a voltage is applied to expand each polymer actuator 25, thereby making the electric prosthetic hand return to the state shown in FIG. 4A.

The first embodiment achieves the following advantages.

(1) Each wire 21 is arranged in a corresponding one of the finger parts 12 and 13, each of which is flexed and extended about the joint sections 15. By winding up the wire 21 by the motor 22, the wire 21 is pulled in the flexing direction to flex each of the finger parts 12 and 13. The polymer actuator 25 is provided to correspond to a part of each wire 21. The locking mechanism A is provided, which restricts relative movement between the wire 21 and the motor 22 after the wire 21 is wound up by the motor 22. The polymer actuator 25 expands and contacts while the locking mechanism A restricts the relative movement, thereby pulling the wire 21 in the flexing direction (FIG. 1).

Thus, the motor 22 is made responsible for largely flexing or displacing the finger parts 12 and 13 in their extended states to a position near a target object. Each polymer actuator 25 is made responsible for grasping a target object with the finger parts 12 and 13. As a result, a target object can be grasped stably while utilizing the benefit of the motor 22, which is capable of largely flexing or displacing the finger parts 12 and 13.

The paying-out mechanism B generates force acting on the wire 21 wound up by the motor 22 and pulled by the polymer actuator 25 in the flexing direction. This force acts to pull the wire 21 in a direction opposite to the flexing direction. Meanwhile, a target object can still be continued to be grasped with the finger parts 12 and 13.

Using the polymer actuators 25 as an auxiliary to the motor 22 allows use of a compact motor such as the motor 22, thereby contributing to weight reduction and reduction in power consumption.

(2) The worm gear mechanism 40 is used as the locking mechanism A. The locking mechanism A permits rotation of the motor 22 in the winding direction while the wire 21 is wound by the motor 22. The locking mechanism A restricts rotation of the motor 22 in a direction opposite to the winding direction after the wire 21 is wound up by the motor 22, thereby restricting relative movement between the wire 21 and the motor 22.

Each polymer actuator 25 is fixed via the attachment parts 34 and 35 to the wire 21. While the wire 21 is wound by the motor 22, each polymer actuator 25 expands in response to application of a voltage (FIGS. 4A and 4B). While the locking mechanism A (the worm gear mechanism 40) restricts relative movement between the wire 21 and the motor 22, application of a voltage is stopped to make each polymer actuator 25 contract (FIG. 4C).

Thus, by winding up the wire 21 around the pulley 16 by the motor 22, each polymer actuator 25 in an expanded state moves in the flexing direction together with the wire 21. This flexes (displaces) the finger parts 12 and 13 largely to a position near a target object.

After the wire 21 is wound up by the motor 22, each polymer actuator 25 contracts while relative movement between the wire 21 and the motor 22 is restricted. This allows a target object to be grasped firmly with the finger parts 12 and 13.

Power is applied to the polymer actuator 25 while the wire 21 is wound by the motor 22. Application of a voltage is stopped after the wire 21 is wound up. This advantageously reduces power consumption if a period when a target object is grasped with the finger parts 12 and 13 is longer than a period when the finger parts 12 and 13 are away from the target object.

(3) The polymer actuator 25 includes the dielectric layer 26 made of an insulating polymer material with elasticity and the electrodes 27 and 28 in a pair, which are made of a conductive polymer material with elasticity and sandwich the dielectric layer 26 from the opposite sides with respect to the thickness direction of the dielectric layer 26 (FIG. 2).

Thus, the dielectric layer 26 can expand along the surface of the dielectric layer 26 in response to application of a voltage between the electrodes 27 and 28. In response to stopping application of a voltage, the dielectric layer 26 can contract along the surface to restore its original shape.

A current continues to flow until charge of a given amount is accumulated in each of the electrodes 27 and 28. Substantially no current flows in response to accumulation of charge of the given amount. This reduces power to be consumed by the behavior (expansion and contraction) of the polymer actuator 25. As a result, a small-capacity battery can be used as the power source 36 (FIGS. 3A and 3B), thereby enhancing convenience.

(4) Winding the dielectric layer 26 and the electrodes 27 and 28 in a spiral pattern forms the principal part of the polymer actuator 25 into a cylindrical shape (FIGS. 3A and 3B).

Such a compact shape (a cylindrical shape) of each polymer actuator 25 improves the mountability of the polymer actuator 25 to the electric prosthetic hand.

In response to application of a voltage, each polymer actuator 25 expands in the axial direction (the longitudinal direction of each polymer actuator 25), which is a direction along the surface of the dielectric layer 26 (FIG. 3B). In response to stopping the voltage application, each polymer actuator 25 contracts in this axial direction (FIG. 3A).

(5) A plurality of polymer actuators 25 is used. Each polymer actuator 25 has movable ends at its opposite end portions. The opposite movable ends of each polymer actuator 25 are attached to the attachment parts 34 and 35 (FIG. 4A).

Compared to use of only one polymer actuator 25, the present embodiment transmits a large force to the wire 21 through the attachment parts 34 and 35, so that a target object can be grasped by a large force of the finger parts 12 and 13.

(6) The polymer actuator 25 used as one of the driving sources for the finger parts 12 and 13 is more lightweight than a driving source made of metal such as a motor or an electromagnetic actuator. This contributes to reduction in the weight of the entire electric prosthetic hand.

(7) A motor may be arranged for each of joint sections in order to flex a finger part with these joint sections. This would increase the weight or complicate the control circuit for the motors.

In this regard, in the first embodiment, only one motor 22 is used while the polymer actuators 25 are used in combination. As described above, the polymer actuator 25 itself is lightweight. This achieves weight reduction in the electric prosthetic hand. Further, the motor 22 can be controlled by a simple circuit.

(8) The dielectric layer 26 of the polymer actuator 25 is made of an insulating polymer material with elasticity and the electrodes 27 and 28 of the polymer actuator 25 are made of a conductive polymer material with elasticity (FIG. 2).

Thus, even if a force acting to extend the finger parts 12 and 13 in their flexed states to move the finger parts 12 and 13 away from a target object is applied from outside, this force can be absorbed by making the polymer actuators 25 expand and contract.

(9) The finger parts 12 and 13 are each formed of a plurality of movable sections 14 and a plurality of joint sections 15. The wire 21 to function as a tendon is arranged in each of the finger parts 12 and 13. The wire 21 is pulled by being wound up by the motor 22 to flex the finger parts 12 and 13.

Thus, unlike a finger part with one joint section, the finger parts 12 and 13 can be flexed to conform to the shape of a target object for grasping the target object. This increases the number of types of a target object that can be grasped.

(10) In an electric prosthetic hand of a type of flexing a finger part by pulling wires, the greater the number of joint sections of the finger part, the greater the amount by which the wire is pulled for flexing the finger part at each joint section.

In this regard, in the first embodiment, the wire 21 to be driven by the motor 22 and the polymer actuator 25 is arranged in each of the finger parts 12 and 13 each having the joint sections 15 so as to pass through these joint sections 15.

Thus, by pulling the wire 21 to a large extent by the motor 22, the finger parts 12 and 13 can be flexed or displaced to a position near a target object. Then, the wire 21 is pulled by the polymer actuator 25. As a result, the target object can be grasped with the finger parts 12 and 13. While utilizing the benefit of the motor 22, which is capable of largely displacing each of the finger parts 12 and 13, the aforementioned advantage (1) of grasping the target object stably can be achieved more effectively.

Second Embodiment

An electric prosthetic hand according to a second embodiment will now be described with reference to FIGS. 1 to 3, and 5. The differences from the first embodiment will be mainly discussed.

Figure 5A:
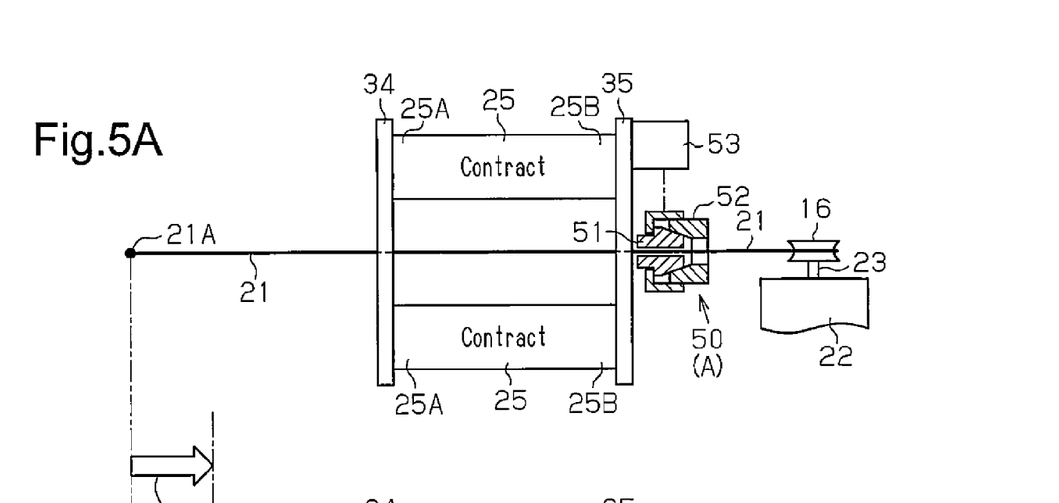
FIGS. 5A to 5C are schematic diagrams showing behavior of an electric prosthetic hand of a second embodiment.

In the first embodiment, the wire 21 is fixed to the attachment parts 34 and 35. In the second embodiment, the wire 21 is arranged to be movable along the length of this wire 21 relative to each polymer actuator 25. More specifically, as shown in FIG. 5A, the wire 21 is arranged to pass through the space between adjacent polymer actuators 25 and the attachment parts 34 and 35 such that the wire 21 can move along the length of this wire 21.

The pulley 16 is attached to the output shaft 23 of the motor 22 such that it can rotate integrally with the output shaft 23.

Each polymer actuator 25 has an end portion 25A that is a fixed end on the side of each of the finger parts 12 and 13 with respect to the axial direction of this polymer actuator 25. Each polymer actuator 25 has an end portion 25B that is a movable end on the side of the motor 22 with respect to the axial direction of this polymer actuator 25.

The attachment part 34 to which the fixed end 25A of each polymer actuator 25 is attached is fixed to the prosthetic hand body 11. The attachment part 34 is not allowed to move relative to the prosthetic hand body 11. The attachment part 35 to which the movable end 25B of each polymer actuator 25 is attached is not fixed to the prosthetic hand body 11. The attachment part 35 is allowed to move in the longitudinal direction of the wire 21 (in the axial direction of the polymer actuator 25) relative to the prosthetic hand body 11.

The locking mechanism A satisfies the following conditions.

Condition 3: to permit relative movement between the wire 21 and each polymer actuator 25 by not securing the wire 21 to the movable end 25B when the wire 21 is wound by the motor 22.

Condition 4: to restrict relative movement between the wire 21 and each polymer actuator 25 by securing the wire 21 to the movable end 25B after the wire 21 is wound up by the motor 22.

In the second embodiment, a collet chuck 50 is used as the locking mechanism A satisfying the Conditions 3 and 4 instead of the worm gear mechanism 40. The collet chuck 50 includes a collet 51, a chuck body 52, and an actuator 53. The collet chuck 50 is arranged near the attachment part 35 on the movable side.

The collet 51 is used for grasping the wire 21 as a workpiece. The collet 51 has a hole formed in a central portion for passage of the wire 21. The collet 51 is provided with cuts extending radially from the passage hole. The collet 51 has an outer circumference provided with a tapered surface that is reduced further in a diameter toward the pulley 16.

The chuck body 52 has a tubular shape with open opposite end portions with respect to the direction of the length of the wire 21. The chuck body 52 is fixed to the attachment part 35. This moves the chuck body 52 together with the movable end 25B in the longitudinal direction of the wire 21 in response to expansion and contraction of the polymer actuator 25. The chuck body 52 has an inner tapered surface that is reduced further in a diameter with a shorter distance to the pulley 16 in conformity with the collet 51.

The actuator 53 is formed of an electromagnetic solenoid, for example. The actuator 53 is coupled to the collet 51 and moves the collet 51 along the length of the wire 21. As the collet 51 is moved to approach the pulley 16 and then enters the chuck body 52, a part of the collet 51 held between adjacent cuts is elastically deformed toward the center, thereby grasping the wire 21. This restricts relative movement between this wire 21 and the movable end 25B of the polymer actuator 25.

When the wire 21 is wound by the motor 22, application of a voltage is stopped to make each polymer actuator 25 contract. After the wire 21 is wound up by the motor 22, a voltage is applied to make each polymer actuator 25 expand while the locking mechanism A restricts relative movement between this wire 21 and the movable end 25B of the polymer actuator 25.

Other than these differences, the second embodiment is the same as the first embodiment. Therefore, like or the same reference numerals are given to those components that are like or the same as the corresponding components of the first embodiment and detailed explanations are omitted.

Operation of the electric prosthetic hand of the second embodiment will now be described.

FIG. 5A shows a state immediately before a target object is grasped with the electric prosthetic hand. In this state, the wire 21 is wound by the motor 22 to a minimum amount. No current is passed through the motor 22. The wire 21 is pulled by the paying-out mechanism B (the wire 45 and the return spring 46) in a direction opposite to the direction in which the motor 22 pulls the wire 21 (the flexing direction). Each of the finger parts 12 and 13 is in an extended state.

The switch 37 is opened to stop application of a voltage between the electrodes 27 and 28 of the polymer actuator 25 (see FIG. 2). In each polymer actuator 25, charge is not accumulated in the electrodes 27 and 28 as a result of discharge. Each polymer actuator 25 is in a contracted state as shown in FIG. 5A. This contraction makes the movable end 25B near the motor 22 approach the fixed end 25A near the finger part 12 or 13. The locking mechanism A does not secure the wire 21 to the movable end 25B but permits relative movement between the wire 21 and each polymer actuator 25. This permits the wire 21 to move in the longitudinal direction of this wire 21 relative to the polymer actuator 25.

To grasp the target object with the electric prosthetic hand in the aforementioned state, the output shaft 23 of the motor 22 is first rotated in one direction integrally with the pulley 16. Then, the wire 21 is wound up around the pulley 16 to pull the wire 21 in the longitudinal direction to the right in the flexing direction of FIG. 5A, thereby moving the wire 21 in the flexing direction. Movement of the wire 21 is transmitted via each joint section 15 to each movable section 14 of each of the finger parts 12 and 13. As a result, the finger parts 12 and 13 are flexed or displaced largely about each joint section 15 to a position near the target object.

Figure 5B:
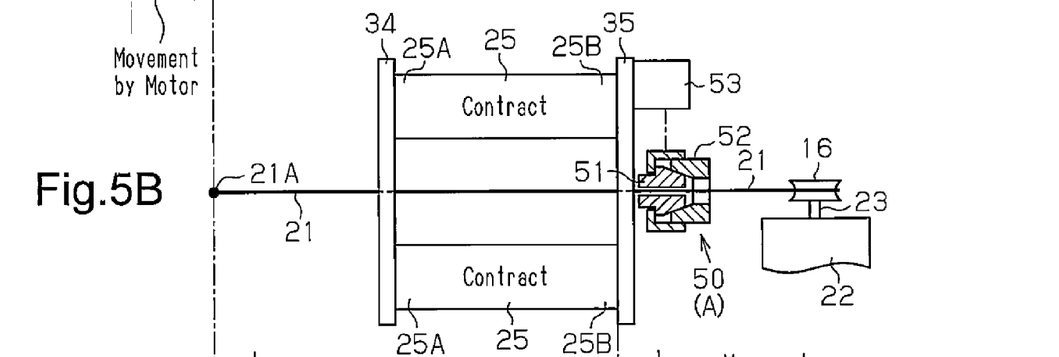
Figure 5C:
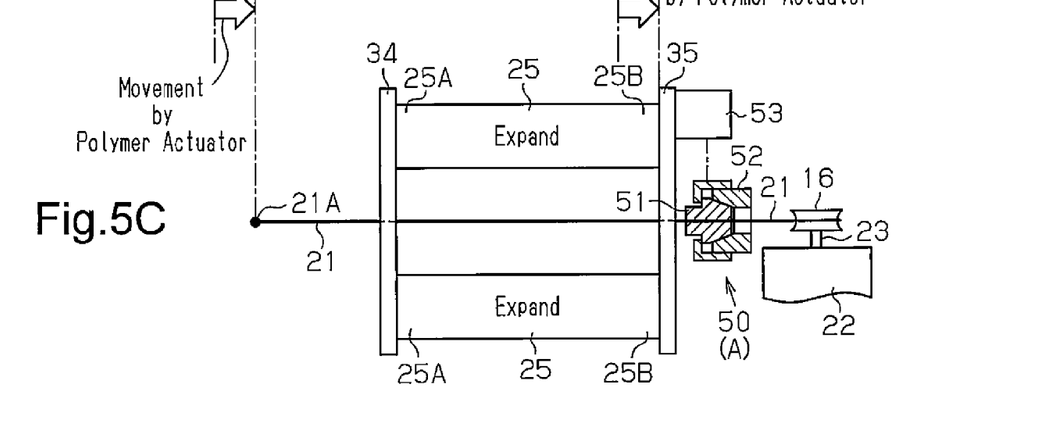

After the wire 21 is wound up around the pulley 16 by the motor 22 to place each of the finger parts 12 and 13 in the aforementioned state, passage of a current through the motor 22 is stopped as shown in FIG. 5B. In response to this stop, the force of pulling the wire 21 in the flexing direction disappears. Meanwhile, after the wire 21 is wound up by the motor 22, the locking mechanism A (the collet chuck 50) secures the wire 21 to the movable end 25B (the attachment part 35) of the polymer actuator 25 as shown in FIG. 5C. This restricts relative movement between the wire 21 and the movable end 25B (the attachment part 35). Thus, the wire 21 wound up around the pulley 16 by the motor 22 is not payed out by the paying-out mechanism B. Additionally, the switch 37 is closed (see FIG. 3B) while relative movement between the wire 21 and the movable end 25B is restricted, thereby applying a voltage between the electrodes 27 and 28 (see FIG. 2) of each polymer actuator 25.

This voltage application makes each polymer actuator 25 expand in the axial direction (the longitudinal direction). In response to this expansion, the movable end 25B moves further away from the fixed end 25A. The attachment part 35, to which the movable end 25B is fixed, also moves in this axial direction together with the locking mechanism A, which secures the wire 21 to the end portion 25B (the movable end). This pulls the wire 21 further in the flexing direction with respect to the longitudinal direction.

The movement of the wire 21 is transmitted via each joint section 15 to each movable section 14 of each of the finger parts 12 and 13, thereby flexing each of the finger parts 12 and 13 about each joint section 15. The finger parts 12 and 13 are pressed against the target object by a strong force, thereby grasping the target object stably.

To move each of the finger parts 12 and 13 away from the target object, the securing of the wire 21 by the locking mechanism A is cancelled. This permits the wire 21 to move relative to each polymer actuator 25. In this state, the motor 22 is rotated in a backward direction opposite to the direction in which the motor 22 rotates for grasping the target object. This rotation weakens the force of the motor 22 of pulling the wire 21. The wire 21 is pulled with the wire 45 and the return spring 46 in a direction opposite to the direction in which the motor 22 pulls the wire 21 (the flexing direction). This extends each of the finger parts 12 and 13 to weaken the force of grasping the target object. As a result, each of the finger parts 12 and 13 moves away from the target object.

The switch 37 is opened in a period from when the aforementioned backward rotation of the motor 22 is started to a point immediately before the target object is grasped with the electric prosthetic hand again. By opening the switch 37, each polymer actuator 25 contracts to make the electric prosthetic hand return to the state shown in FIG. 5A.

Thus, the second embodiment has the same advantages as the above described advantages (1), (3), (4), and (6) to (10) of the first embodiment. In addition, the second embodiment has the following advantage (11) in place of the advantage (2). In the second embodiment, a plurality of polymer actuators 25 are used and only one end portion 25B of each polymer actuator 25 in the longitudinal direction is formed as a movable end. The respective movable ends thereof are attached to the common attachment part 35. This achieves an advantage equivalent to the aforementioned advantage (5). This applies to a third embodiment discussed below.

(11) In the second embodiment, the wire 21 is arranged to be movable along the length of this wire 21 relative to each polymer actuator 25. In each polymer actuator 25, the end portion 25A near the finger part 12 or 13 with respect to the axial direction is a fixed end and the end portion 25B near the motor 22 is a movable end.

The collet chuck 50 is used as the locking mechanism A. When the wire 21 is wound up by the motor 22, the wire 21 is not secured to the end portion 25B (the movable end) to permit relative movement between the wire 21 and each polymer actuator 25. After the wire 21 is wound up by the motor 22, the wire 21 is secured to the end portion 25B (the movable end) to restrict relative movement between the wire 21 and each polymer actuator 25.

When the wire 21 is wound by the motor 22, each polymer actuator 25 contracts in response to stopping application of a voltage (FIGS. 5A and 5B). When the locking mechanism A (the collet chuck 50) restricts relative movement between the wire 21 and each polymer actuator 25, each polymer actuator 25 expands in response to application of a voltage (FIG. 5C).

Thus, by winding up the wire 21 around the pulley 16 by the motor 22, the finger parts 12 and 13 can be flexed or displaced largely to a position near a target object.

After the wire 21 is wound up by the motor 22, each polymer actuator 25 expands while the locking mechanism A (the collet chuck 50) secures the wire 21 to the end portion 25B (the movable end). This allows the target object to be grasped firmly with the finger parts 12 and 13.

Application of a voltage to the polymer actuator 25 is stopped when the wire 21 is wound by the motor 22. A voltage is applied to the polymer actuator 25 after the wire 21 is wound up. This advantageously reduces power consumption if the period during which the finger parts 12 and 13 are away from a target object is longer than the period during which the target object is grasped with the finger parts 12 and 13.

Third Embodiment

An electric prosthetic hand according to a third embodiment will now be described with reference to FIGS. 1 to 3, and 6. The differences from the second embodiment will be mainly discussed.

Figure 6A:
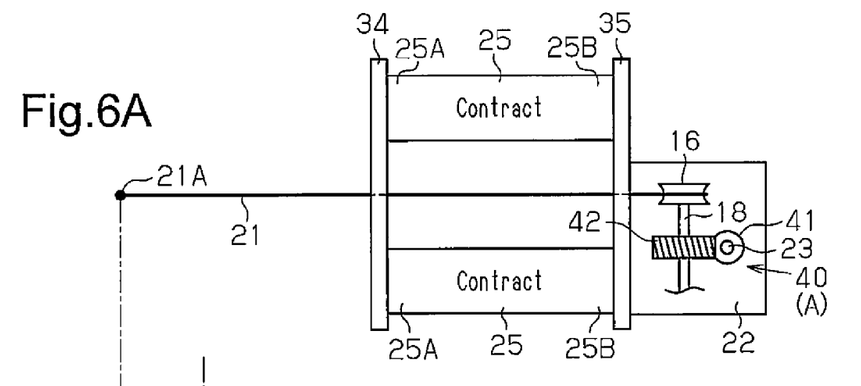
FIGS. 6A to 6C are schematic diagrams showing behavior of an electric prosthetic hand of a third embodiment.

As shown in FIG. 6A, in the third embodiment, the motor 22, the locking mechanism A, and the pulley 16 are provided at the movable end 25B of each polymer actuator 25. This makes the motor 22 movable along the length of the wire 21 relative to the prosthetic hand body 11.

As in the first embodiment, the locking mechanism A of the third embodiment is formed of the worm gear mechanism 40 including the worm 41 and the worm wheel 42. Unlike the second embodiment, the collet chuck 50 is not used. The locking mechanism A of the third embodiment functions in the same way as the locking mechanism A of the first embodiment.

When the wire 21 is wound by the motor 22, application of a voltage to each polymer actuator 25 is stopped. This makes each polymer actuator 25 contract. After the wire 21 is wound up by the motor 22, a voltage is applied to each polymer actuator 25 while the locking mechanism A restricts relative movement between the wire 21 and the motor 22. This voltage application makes each polymer actuator 25 expand. This expansion moves the motor in the flexing direction.

Other than these differences, the third embodiment is the same as the second embodiment. Therefore, like or the same reference numerals are given to those components that are like or the same as the corresponding components of the second embodiment and detailed explanations are omitted.

Operation of the electric prosthetic hand of the third embodiment will now be described.

FIG. 6A shows a state immediately before a target object is grasped with the electric prosthetic hand. In this state, the wire 21 is wound up by the motor 22 to a minimum amount. No current is passed through the motor 22. The wire 21 is pulled by the paying-out mechanism B (the wire 45 and the return spring 46) in a direction opposite to the direction in which the motor 22 pulls the wire 21 (the flexing direction). Each of the finger parts 12 and 13 is in an extended state.

The switch 37 is opened to stop application of a voltage between the electrodes 27 and 28 of the polymer actuator 25 (see FIG. 2). In each polymer actuator 25, charge is not accumulated in the electrodes 27 and 28 as a result of discharge. Each polymer actuator 25 is in a contracted state as shown in FIG. 6A. This contraction makes the movable end 25B near the motor 22 approach the fixed end 25A near the finger part 12 or 13. The wire 21 is not fixed to each polymer actuator 25 (the attachment parts 34 and 35) and movable along the length of the wire 21 relative to each polymer actuator 25 (the attachment parts 34 and 35). The motor 22 can move along the length of the wire 21 relative to the prosthetic hand body 11.

To grasp the target object with the electric prosthetic hand in the aforementioned state, the motor 22 is first used as a driving source. At this time, the locking mechanism A (the worm gear mechanism 40) permits rotation of the output shaft 23 in a direction for winding the wire 21.

When the output shaft 23 of the motor 22 is rotated, the rotation is transmitted via the worm gear mechanism 40 (the worm 41 and the worm wheel 42) to the rotary shaft 18. This rotates the pulley 16 together with the rotary shaft 18 in one direction to wind up the wire 21 around the pulley 16. Then, the wire 21 is pulled to the right in the flexing direction of FIG. 6A in the longitudinal direction. At this time, the polymer actuator 25 continues to contract. This moves the wire 21 along its length and in the flexing direction.

The movement of the wire 21 is transmitted via each joint section 15 to each movable section 14 of each of the finger parts 12 and 13. The finger parts 12 and 13 are flexed or displaced largely about each joint section 15 to a position near the target object.

Figure 6B:
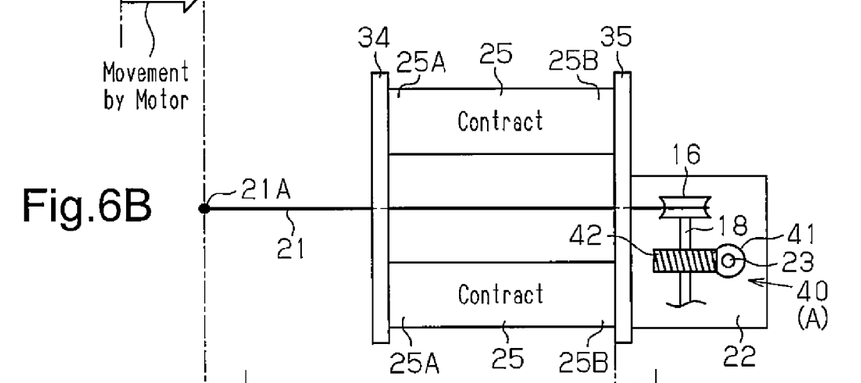
Figure 6C:
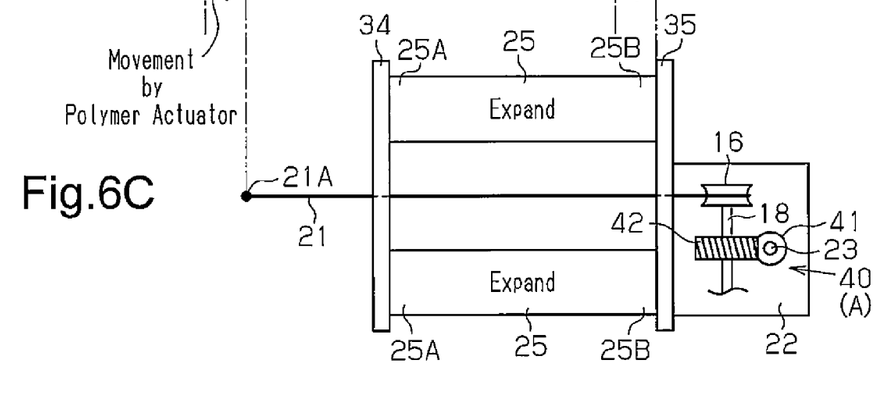

After the wire 21 is wound up around the pulley 16 by the motor 22 to place each of the finger parts 12 and 13 in the aforementioned state, passage of a current through the motor 22 is stopped as shown in FIG. 6B. In response to this stop, the force of pulling the wire 21 in the flexing direction disappears. Meanwhile, force generated by the paying-out mechanism B (the wire 45 and the return spring 46), specifically, force of pulling the wire 21 in a direction opposite to the direction in which the motor 22 pulls the wire 21 (the flexing direction) acts on the wire 21. At this stage, however, as shown in FIG. 6C, the locking mechanism A (the worm gear mechanism 40) restricts rotation of the motor 22 in a direction opposite to the winding direction, thereby restricting relative movement between the wire 21 and the motor 22. Thus, the wire 21 is not payed out from the pulley 16 even when passage of a current through the motor 22 is stopped. As a result, the wire 21 is kept in a position where the wire 21 is wound up by the motor 22.

Under the aforementioned circumstance, where the worm gear mechanism 40 restricts relative movement between the wire 21 and the motor 22, the switch 37 is closed (see FIG. 3B) to apply a voltage between the electrodes 27 and 28 of each polymer actuator 25 (see FIG. 2). This voltage application makes each polymer actuator 25 expand in the axial direction (the longitudinal direction).

Each polymer actuator 25 expands in response to movement of the movable end 25B to separate farther from the fixed end 25A and to approach the motor 22. The attachment part 35, to which the end portion 25B (the movable end) is fixed, also moves toward the motor 22 together with the locking mechanism A. This moves the motor 22 in the flexing direction. As a result, the wire 21 is pulled further in the flexing direction.

The movement of the wire 21 is transmitted via each joint section 15 to each movable section 14 of each of the finger parts 12 and 13 to flex each of the finger parts 12 and 13 about each joint section 15. Then, the finger parts 12 and 13 are pressed against the target object by a strong force, thereby grasping the target object stably.

To move each of the finger parts 12 and 13 away from the target object, the output shaft 23 of the motor 22 is rotated in a backward direction opposite to the direction in which the output shaft 23 rotates for grasp of the target object. This rotation weakens the force of the motor 22 of pulling the wire 21. The wire 21 is pulled by the paying-out mechanism B (the wire 45 and the return spring 46) in a direction opposite to the direction in which the motor 22 pulls the wire 21. This extends each of the finger parts 12 and 13 to weaken the force of grasping the target object. As a result, each of the finger parts 12 and 13 moves away from the target object.

The switch 37 is opened in a period from when the backward rotation of the motor 22 is started to a point immediately before a target object is grasped with the electric prosthetic hand. By opening the switch 37, each polymer actuator 25 contracts to make the electric prosthetic hand return to the state shown in FIG. 6A.

Thus, the third embodiment has the same advantages as the advantages (1), (3), (4), and (6) to (10) of the first embodiment. In addition, the third embodiment has the following advantage (12) in place of the advantage (2).

(12) The wire 21 is arranged to be movable along the length of this wire 21 relative to each polymer actuator 25. The motor 22 is arranged to be movable along the length of the wire 21. In each polymer actuator 25, the end portion 25A near the finger part 12 or 13 is a fixed end and the end portion 25B near the motor 22 is a movable end.

The worm gear mechanism 40 is used as the locking mechanism A. When the wire 21 is wound by the motor 22, rotation of the motor 22 in the winding direction is permitted. After the wire 21 is wound up by the motor 22, rotation of the motor 22 in a direction opposite to the winding direction is restricted to restrict relative movement between the wire 21 and the motor 22.

When the wire 21 is wound by the motor 22, each polymer actuator 25 contracts in response to stopping application of a voltage (FIGS. 6A and 6B). While the locking mechanism A (the worm gear mechanism 40) restricts relative movement between the wire 21 and each polymer actuator 25, each polymer actuator 25 expands in response to application of a voltage. This expansion moves the motor 22 in the flexing direction (FIG. 6C).

Thus, by winding up the wire 21 around the pulley 16 by the motor 22, the finger parts 12 and 13 can be flexed or displaced largely to a position near a target object.

After the wire 21 is wound up by the motor 22, each polymer actuator 25 expands while the locking mechanism A restricts rotation of the motor 22 in a direction opposite to the winding direction. This pulls the wire 21 in the flexing direction, so that a target object can be grasped firmly with the finger parts 12 and 13.

Application of a voltage to the polymer actuator 25 is stopped when the wire 21 is wound up by the motor 22. A voltage is applied to the polymer actuator 25 after the wire 21 is wound up. This advantageously reduces power consumption if the period during which the finger parts 12 and 13 are away from a target object is longer than the period during which the target object is grasped with the finger parts 12 and 13.

The above described embodiments may be modified as follows.

Regarding Finger Parts 12, 13

The aforementioned electric prosthetic hand is further applicable to an electric prosthetic hand with three or more finger parts including the finger parts 12 and 13. A target object can be grasped more stably with a larger number of finger parts including the finger parts 12 and 13.

The aforementioned electric prosthetic hand is further applicable to an electric prosthetic hand with the finger parts 12 and 13 each having different numbers of the movable sections 14 and the joint sections 15 from those of the first to third embodiments. The finger parts 12 and 13 each having a larger number of movable sections 14 and a larger number of joint sections 15 can be flexed to conform to the shape of a target object, so that the target object can be grasped more stably.

The minimum number of the movable sections and that of the joint sections in each finger part are both one. Even in this case, the aforementioned advantage (1) can be achieved.

Meanwhile, the advantage of grasping a target object stably while utilizing the benefit of a motor which is capable of displacing a finger part largely, becomes more significant if at least one of finger parts has two or more joint sections. This is because the greater the number of joint sections, the greater the amount by which a wire needs to be pulled for flexing a finger part at each joint section. In this case, by pulling the wire by the motor to a large amount, the finger parts can be flexed or displaced to a position near a target object. The wire is then pulled by a polymer actuator, thereby allowing the target object to be grasped with the finger parts.

Regarding Polymer Actuator 25

The polymer actuator 25 may be of an ionic type instead of the aforementioned dielectric type.

An ionic polymer actuator is formed of an ion-exchange resin and an electrode bonded to each other. A polymer actuator of this type is typically formed by bonding an electrode made of precious metal such as gold or platinum to each of opposite sides of a fluorine-based ion-exchange resin film by electroless plating. In this polymer actuator, a voltage of some volts is applied between the electrodes to cause movement of ions inside the ion-exchange resin. As a result, cations move toward a cathode, for example. This movement of the ions generates a difference in swelling between the front side and the back side of the polymer actuator to elastically deform the polymer actuator. When application of the voltage is stopped, the polymer actuator restores its original shape using its elastic resilience. Such elastic deformation and restoration make the polymer actuator expand and contract.

Regarding Force of Finger Parts 12, 13 for Grasping Target Object

This force can be changed by controlling the following elements.

(i) The voltage applied to the electrodes 27 and 28 of each polymer actuator 25. Increasing the voltage increases the aforementioned grasping force.

(ii) The diameter of the polymer actuator 25.

Increasing the diameter increases the aforementioned grasping force.

(iii) The number of polymer actuators 25 to expand and contract. Increasing this number increases the aforementioned grasping force.

In this case, the number of polymer actuators 25 to be attached to the electric prosthetic hand may be changed. Alternatively, the number of polymer actuators 25 to be targeted for application of a voltage may be changed by control or by manipulation depending on the situation.

Regarding Motor 22

The motor 22 may be provided for each of the finger parts 12 and 13.

In the third embodiment, the motor 22, the locking mechanism A (the worm gear mechanism 40), the pulley 16 and others may be provided to the prosthetic hand body 11 to be movable along the length of the wire 21 while being separated from each polymer actuator 25. In this case, the motor 22 and the like are arranged near the movable end 25B and the attachment part 35 of each polymer actuator 25. This is intended to move the motor 22 and the like using each polymer actuator 25, which expands.

Regarding Locking Mechanism a

The locking mechanism A may be formed of a member different from the worm gear mechanism 40 and the collet chuck 50 as long as this member can restrict relative movement between the wire 21 and one of the motor 22 and the polymer actuator 25 after the wire 21 is wound up by the motor 22.

The invention claimed is:

1. An electric prosthetic hand comprising:
 a plurality of finger parts, each of which is flexed and extended about a joint section;
 a wire arranged along each of the finger parts while passing through the joint section;
 a motor that winds up the wire to pull the wire along a length of the wire in a direction of flexing, thereby flexing the finger part;
 a polymer actuator formed of a polymer material into an elongated shape and arranged to correspond to a part of the wire, wherein the polymer actuator expands and contracts in an axial direction by being deformed elastically in response to application of a voltage and restoring its original shape in response to stopping the application of the voltage; and
 a locking mechanism that restricts relative movement between the wire and one of the motor and the polymer actuator after the wire is wound up by the motor,
 wherein the polymer actuator expands and contracts when the locking mechanism restricts the relative movement, thereby pulling the wire in the flexing direction.

2. The electric prosthetic hand according to claim 1, wherein:
 the locking mechanism permits rotation of the motor in a winding direction when the wire is wound by the motor and restricts relative movement between the wire and the motor by restricting rotation of the motor in a direction opposite to the winding direction after the wire is wound up by the motor,
 the polymer actuator is fixed to the wire, and
 the polymer actuator is expanded when the wire is wound by the motor and is contracted when the locking mechanism restricts the relative movement.

3. The electric prosthetic hand according to claim 1, wherein:
 the wire is arranged to be movable along the length of the wire relative to the polymer actuator,
 the polymer actuator has a fixed end at an end portion near the finger part with respect to the axial direction and a movable end at an end portion near the motor with respect to the axial direction,
 the locking mechanism permits relative movement between the wire and the polymer actuator by not securing the wire to the movable end when the wire is wound by the motor,
 the locking mechanism restricts relative movement between the wire and the polymer actuator by securing the wire to the movable end after the wire is wound up by the motor, and
 the polymer actuator is contracted when the wire is wound by the motor and is expanded when the locking mechanism restricts the relative movement.

4. The electric prosthetic hand according to claim 1, wherein:
 the wire is arranged so as to be movable along the length of the wire relative to the polymer actuator,
 the motor is arranged to be movable along the length of the wire,
 the polymer actuator has a fixed end at an end portion near the finger part with respect to the axial direction and a movable end at an end portion near the motor with respect to the axial direction,
 the locking mechanism permits rotation of the motor in a direction of winding when the wire is wound up by the motor,
 the locking mechanism restricts relative movement between the wire and the motor by restricting rotation of the motor in a direction opposite to the winding direction after the wire is wound up by the motor,
 the polymer actuator is contracted when the wire is wound by the motor, and
 the polymer actuator is expanded when the locking mechanism restricts the relative movement, and the expansion of the polymer actuator moves the motor in the flexing direction.

5. The electric prosthetic hand according to claim 1, wherein:
 the polymer actuator includes a dielectric layer made of an insulating polymer material with elasticity and electrodes in a pair that are made of a conductive polymer material with elasticity and sandwich the dielectric layer from opposite sides, and
 the polymer actuator expands and contracts by expanding the dielectric layer along a surface of the dielectric layer in response to application of a voltage between the electrodes and contracting the dielectric layer to restore its original shape in response to stopping the voltage application.

6. The electric prosthetic hand according to claim 5, wherein:
 the polymer actuator is formed into a cylindrical shape by winding the dielectric layer and the electrodes in a spiral pattern, and
 the polymer actuator expands in the axial direction in response to application of a voltage between the electrodes and contracts in the axial direction in response to stopping the voltage application to restore its original shape.

7. The electric prosthetic hand according to claim 6, wherein:

the polymer actuator is one of a plurality of polymer actuators, and the movable ends of the polymer actuators are attached to a common attachment part.

8. The electric prosthetic hand according to claim 1, wherein:

at least one of the finger parts has a plurality of joint sections, and the wire, which is driven by the motor and the polymer actuator, is arranged in the finger part with the joint sections while passing through the joint sections.

* * * * *